United States Patent
Zillner et al.

(10) Patent No.: US 8,965,818 B2
(45) Date of Patent: Feb. 24, 2015

(54) METHOD AND SYSTEM FOR SUPPORTING A CLINICAL DIAGNOSIS

(75) Inventors: Sonja Zillner, München (DE); Heiner Oberkampf, München (DE)

(73) Assignee: Siemens Aktiengesellschaft, Munich (DE)

( * ) Notice: Subject to any disclaimer, the term of this patent is extended or adjusted under 35 U.S.C. 154(b) by 268 days.

(21) Appl. No.: 13/473,134

(22) Filed: May 16, 2012

(65) Prior Publication Data

US 2013/0310653 A1 Nov. 21, 2013

(51) Int. Cl.
| | |
|---|---|
| G06F 15/18 | (2006.01) |
| G06F 17/00 | (2006.01) |
| G06N 7/00 | (2006.01) |
| G06N 7/08 | (2006.01) |
| G06N 5/04 | (2006.01) |
| G06N 5/00 | (2006.01) |
| G06F 19/00 | (2011.01) |

(52) U.S. Cl.
CPC ............... *G06N 5/00* (2013.01); *G06F 19/345* (2013.01)
USPC .................. 706/14; 706/55; 706/59; 706/60

(58) Field of Classification Search
None
See application file for complete search history.

(56) References Cited

U.S. PATENT DOCUMENTS

| | | | |
|---|---|---|---|
| 6,468,210 B1 * | 10/2002 | Iliff | 600/300 |
| 6,524,241 B2 * | 2/2003 | Iliff | 600/300 |
| 6,527,713 B2 * | 3/2003 | Iliff | 600/300 |
| 7,392,199 B2 * | 6/2008 | Karlov et al. | 705/2 |
| 2003/0144580 A1 * | 7/2003 | Iliff | 600/300 |
| 2009/0007924 A1 * | 1/2009 | Iliff | 128/898 |
| 2009/0157663 A1 * | 6/2009 | Kate | 707/5 |
| 2011/0098193 A1 * | 4/2011 | Kingsmore et al. | 506/9 |
| 2011/0106821 A1 * | 5/2011 | Hassanzadeh et al. | 707/749 |

OTHER PUBLICATIONS

Berner, Eta S. Clinical Decision Support Systems. Springer Science+ Business Media, LLC, 2007.*
Lucas, P. J. F., H. Boot, and B. G. Taal. "Computer-based decision support in the management of primary gastric non-Hodgkin lymphoma." Methods of information in medicine 37 (1998): 206-219.*

(Continued)

*Primary Examiner* — Kakali Chaki
*Assistant Examiner* — Daniel Pellett
(74) *Attorney, Agent, or Firm* — King & Spalding L.L.P.

(57) ABSTRACT

Methods and systems may support conclusions of a clinician by enabling the clinician to arbitrarily define the symptoms according to the patient's record. The method may comprise: (a) determining a plurality of symptoms representing a patient and including characteristics of the patient, the symptoms being categorized as present symptoms, absent symptoms or open symptoms; (b) establishing a multi-tier relationship between said symptoms and a plurality of diseases based on a knowledge model; (c) adjusting weighting factor(s) for at least one multi-tier relationship based on said knowledge model; (d) optionally adjusting at least one weighting factor of step (c) by an expert; and (e) building a ranking of diseases from said multi-tier relationship based on said weighting factors. The method may provide an efficient ranking of disease information, thereby supporting a clinical diagnosis that may consider multiple symptoms while emphasizing particular symptoms in view of the clinician's expertise.

6 Claims, 2 Drawing Sheets

(56) References Cited

OTHER PUBLICATIONS

Croitoru, Madalina, et al. "Conceptual Graphs based information retrieval in HealthAgents." Computer-Based Medical Systems, 2007. CBMS'07. Twentieth IEEE International Symposium on. IEEE, 2007.*

Szolovits, Peter. "Uncertainty and decisions in medical informatics." Methods of Information in Medicine-Methodik der Information in der Medizin 34.1 (1995): 111-121.*

* cited by examiner

METHOD AND SYSTEM FOR SUPPORTING A CLINICAL DIAGNOSIS

TECHNICAL FIELD

The disclosure provides methods and systems for supporting a clinical diagnosis.

BACKGROUND

Clinical diagnosis systems aided by artificial intelligence are well known in the art. Although theoretical foundation and practical application of such diagnosis systems have evolved through many years, there is still a lack of acceptance by clinicians leading to a rare usage of such systems.

A particular reason for this lacking acceptance is due to the fact that known diagnosis systems are designed with the aim of delivering an entire diagnosis which is able to explain all symptoms.

This holistic approach, however, often leads to a resulting diagnosis based on detailed and vast disease-sets which is far away from meeting the requirements of clinicians.

Instead of delivering a specific multi-fault diagnosis based on multiple symptoms it would be more beneficial to deliver a single-fault diagnosis. However, a single disease itself cannot entirely "explain" all symptoms.

SUMMARY

In one embodiment, a method for supporting a clinical diagnosis comprises (a) determining a plurality of symptoms representing a patient, the symptoms including characteristics of the patient, wherein each symptom is categorized as a present symptom, an absent symptom, or an open symptom; (b) establishing a multi-tier relationship between said plurality of symptoms and a plurality of diseases; (c) adjusting at least one weighting factor for at least one of said multi-tier relationship and/or symptom based on a knowledge model; (d) optionally adjusting at least one weighting factor of step (c) by an expert; and (e) building a ranking of diseases from said multi-tier relationship based on said weighting factors.

In a further embodiment, said multi-tier relationship between said plurality of symptoms and said plurality of diseases is implemented by a bipartite graph, the bipartite graph including a plurality of nodes with each node assigned to a symptom or disease, the bipartite graph including a plurality of edges expressing a particular relationship between a particular symptom and a particular disease. In a further embodiment, said weighting factors include a consideration of a patient-specific incidence of a disease, a strength of a disease-symptom relation and/or an importance of a symptom.

In another embodiment, a system for supporting a clinical diagnosis comprises: a semantic patient record module including semantically annotated symptoms representing a patient, the symptoms including characteristics of the patient, the symptoms being categorized as present symptoms, absent symptoms or open symptoms; a weighted disease-symptom module including a knowledge model establishing a multi-tier relationship between said plurality of symptoms and a plurality of diseases; the weighted disease-symptom module for adjusting at least one weighting factor for at least one of said multi-tier relationship and/or for at least one symptom on the basis of a medical ontology module; a user interaction module for optionally adjusting at least one weighting factor by an expert; and the weighted disease-symptom module for building a ranking of diseases from said multi-tier relationship weighted by said weighting factors. In addition, the disease-symptom models may represent the mentioned context parameters as dedicated weighting factors within the model, In another embodiment, a computer program product contains a program code stored on a computer-readable medium and which, when executed on a computer, carries out any of the methods disclosed above.

In another embodiment, a data storage carrier that stores a computer program to cause a computer to perform any of the methods disclosed above.

BRIEF DESCRIPTION OF THE DRAWINGS

Example embodiments will be explained in more detail below with reference to figures, in which.

DETAILED DESCRIPTION

Figure 1:
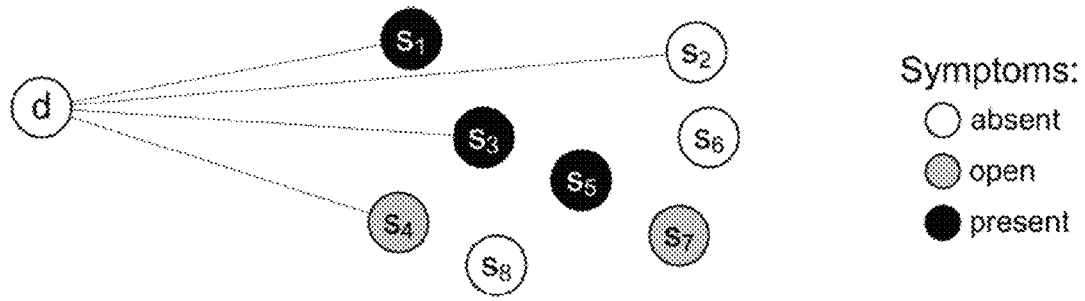
FIG. 1 shows a schematic representation of a multi-tier relationship between a plurality of symptoms and a plurality of diseases.

Some embodiments provide a method for supporting a clinical diagnosis which is capable of considering multiple symptoms while at the same time being flexible enough to emphasize certain symptoms in view of the clinician's expertise.

According to one embodiment, a method for supporting a clinical diagnosis is provided, the method including the steps of:

a) determining a plurality of symptoms representing a patient, the symptoms including characteristics of the patient, the symptoms being categorized as present symptoms, absent symptoms or open symptoms;

b) establishing a multi-tier relationship between said plurality of symptoms and a plurality of diseases on the basis of a knowledge model;

c) adjusting at least one weighting factor for at least one of said multi-tier relationship on the basis of said knowledge model;

d) optionally adjusting at least one weighting factor of step c) by an expert;

e) building a ranking of diseases from said multi-tier relationship based on said weighting factors.

In order to approach a diagnosis, i.e., suggesting a probable set of diseases being the cause for some or all of the symptoms determined in the first step of the method, a multi-tier relationship between said plurality of symptoms and a plurality of diseases is established on the basis of a knowledge model. The knowledge model encompasses medical ontologies providing structural and relational information about medical diseases and symptoms enabling the establishment of a multitude ("multi-tier") of initial relationships between the symptoms and diseases.

In a further step of the method, weighting factors for at least one of said multi-tier relationship on the basis of said knowledge model may be adjusted. A weighting factor basically describes a relatedness of a particular symptom to a particular disease. Using a knowledge model capturing not only information about a relationship between symptoms and diseases but as well capturing a representation of various weight factors may advantageously provide that the initial multi-tier relationship is adjusted in a way which eventually leads to a ranking of likely diseases.

Figuratively speaking, the individual set of symptoms of a current patient could be conceived as a centre encompassed by a cloud of multi-tier relationships to possible diseases. Adjusting the weighting factors means that some diseases of the cloud of multi-tier relationships around the centre of patient's symptoms move closer in the ranking of likely diseases eventually explaining the patient's symptoms.

The method may rely on a formal knowledge model and an extended information retrieval algorithm which may allow context-sensitive ranking of clinical data by seamlessly incorporating symptoms and further characteristics of the patient.

The method may advantageously extend the classical information retrieval approach by applying weighting factors of a knowledge model in order to infer the rank of likely diseases. Some embodiments provide an optional adjusting by an expert which allows the expert—by simply altering weighting factors—to fine-tune the ranking by incorporating her or his expertise and experience knowledge. An optional adjustment of at least one weighting factor by an expert aims a further rectification of the ranking of diseases. An expert, e.g., a clinician, may be enabled to influence the result using her or his expertise and experience knowledge. The influence is applied on the weighting factor, for example in order to test alternative results. By increasing a weighting factor assigned to a specific symptom, the influence of the specific symptom is emphasized. As correct weighting of symptoms, i.e., determining the relevance of symptoms in a particular context largely depends on the clinician's intuition, the ability of weighting of symptoms, beyond registering the intensity, may be important to the diagnosis.

The method may advantageously support conclusions of a clinician by enabling her or him to arbitrarily define the symptoms according to the patient's record. This approach entails a departure from the traditional multi-fault diagnosis based on multiple symptoms. As a matter of fact, the traditional approach necessitated the clinician to map a present set of patient symptoms to a similar set of symptoms on record.

Applying the method, an efficient ranking of disease information may be accomplished, thereby supporting a clinical diagnosis which is capable of considering multiple symptoms while at the same time being flexible enough to emphasize certain symptoms in view of the clinician's expertise.

According to one embodiment of the method said multi-tier relationship between said plurality of symptoms and said plurality of diseases may be implemented by a bipartite graph, the bipartite graph including a plurality of nodes with each node assigned to a symptom or disease, the bipartite graph including a plurality of edges expressing a particular relationship between a particular symptom and a particular disease.

According to a further embodiment of the method, said weighting factors may include a consideration of a patient-specific incidence of a disease, a strength of a disease-symptom relation and/or an importance of a symptom.

According to a further embodiment, a system for supporting a clinical diagnosis is provided, the system comprising:
  a semantic patient record module including semantically annotated symptoms representing a patient, the symptoms including characteristics of the patient, the symptoms being categorized as present symptoms, absent symptoms or open symptoms;
  a weighted disease-symptom module including a knowledge model establishing a multi-tier relationship between said plurality of symptoms and a plurality of diseases;
  the weighted disease-symptom module for adjusting at least one weighting factor for at least one of said multi-tier relationship and/or for at least one symptom on the basis of a medical ontology module;
  a user interaction module for optionally adjusting at least one weighting factor by an expert
  In addition, the disease-symptom models represent the mentioned context parameters as dedicated weighting factors within the model,
  the weighted disease-symptom module for building a ranking of diseases from said multi-tier relationship weighted by said weighting factors.

The system disclosed herein may include a weighted disease-symptom knowledge model which captures the information about the relationship between symptom and diseases as well as weighting factor that influence the ranking of the disease information.

The clinical decision making is a complex process relying on a context-sensitive interpretation of various knowledge resources and information.

There are several high-level requirements that need to be addressed by clinical decision support systems. Firstly, such systems need to reflect and incorporate detailed information from different medical and clinical disciplines. Secondly, within the clinical decision process, missing and incomplete information needs to be handled efficiently. And thirdly, situation and context-dependent information needs to be incorporated into the clinical decision making. For instance, with additional information being available in the process of diagnose the interpretation of clinical data needs to incorporate this new information and adjust the interpretation of data accordingly. New information may include a new examination result that contributes to a deeper understanding of a particular clinical problem or the opinion of an expert of a different medical domain.

A variety of formalisms and techniques are implemented in known clinical diagnosis systems, including set-cover, abductive reasoning, logic approaches, Bayesian networks, rule-based systems, case-based reasoning etc.

Most of the logical approaches aim to explain a whole set of clinical observations, i.e., provide a complete diagnosis. This holistic approach, however, leads to diagnosis consisting of large fault sets and thus unspecific and redundant diagnosis, which are not really suitable to help the clinician. Often diagnosis-algorithms optimize the set of faults contained in a diagnosis under consideration of so called parsimony criteria. In set-cover those are, e.g., minimal cardinality, irredundancy, relevance, most probable diagnosis and minimal cost.

Since Bayes-nets are best suited for diagnosis they are successfully implemented in some expert systems. However Bayes-nets require statistical knowledge, which is not broadly available. Even the a-priori probabilities for signs and symptoms P(s) are mostly not known. In those cases one cannot use systems based on Bayes-nets to compute the conditional probability for a disease with the help of the Bayes-Theorem.

The method according to one embodiment, in turn, follows a different approach which is generally based on a context-sensitive ranking algorithm for disease information. The overall goal of the algorithm is to provide the clinician the most relevant information in the context of establishing a diagnosis for one particular patient.

Embodiments of the method may identify the most likely disease for a given patient being represented by a set of symptoms with clinical evidence. The determination of a plurality of symptoms may include characteristics of the patient, which hereinafter are accordingly subsumed under the term "symptoms". These characteristics of the patient may include the patient's age, the patient's gender, the patient's lifestyle habits, e.g., consumption of alcohol, tobacco products, etc.

In some cases, not only present symptoms are of interest, but also absent symptoms. As absent symptoms allow clinicians to exclude certain diseases, they are of similar importance in the diagnosis process. Open symptoms, i.e., symptoms, which have not been investigated yet, are also addressed by the method in order to ensure a certain flexibility by using a place-holder within the process of establishing a diagnosis. Should new examination needs emerge in the course of this diagnosis process, these open symptoms may be verified or falsified by further medical investigation of the patient without the need to alter the definition of the symptoms. The plurality of symptoms is eventually organized in semantically annotated data.

In a further step, the method may provide an establishment of a multi-tier relationship between the plurality of the patient's symptoms and a plurality of diseases. This step basically captures a semantic relationship between diseases and the semantically annotated symptom data of the previous step.

In a further step, the method may provide an adjustment of at least one weighting factor for at least one of said multi-tier relationship on the basis of a knowledge model, the knowledge model formally representing knowledge originating from various different classical medical knowledge resources capturing knowledge about diseases and underlying symptoms. Such disease-symptom models readily include context parameters as dedicated weighting factor within a weighted disease-symptom model. According to one embodiment of the method, the following context parameters determine a ranking of a disease:

Information about disease-specific Factors, such as age, gender-specific incidence proportions, etc;
Information about disease-symptom relationships, such as an information about leading symptom and information about a high correlation between diseases and symptoms; and;
Information about symptom-specific factors, such as the novelty or the intensity of symptoms as well as the clinician's expert evaluation about the importance of specific symptoms in the context of a particular diagnose.

The latter symptom-specific factors can be optionally adjusted by an expert, e.g., a clinician, in terms of importance of specific symptoms in the context of a particular patient while interacting with the diagnose system.

These three context factors are formally modelled and represented within the dedicated weighted disease-symptom model. According to one embodiment, the weighted disease-symptom model is represented as bipartite graph structure with weighted edges and nodes, which will be described hereafter.

In a final step of the method a ranking of diseases from said multi-tier relationship weighted by said weighting factors may be established.

The weighted disease-symptom model may be represented as bipartite graph structure. Hereby, weighted nodes represent diseases and symptoms, and edges in between the nodes represent a correlation between diseases and symptom concepts.

Turning now to FIG. 1 which shows a schematic representation of a multi-tier relationship between a plurality of symptoms $s_1, s_2, \ldots, s_8$ and a plurality of diseases, for which only one representative disease d is shown. In other words, the schematic representation shows a matching of a typical symptomatology of a disease d with a set of patient's symptoms $s_1, s_2, \ldots, s_8$.

FIG. 1 does not yet show a use of weighting factors, which are formally introduced in the following.

A set of diseases is given by:

$$D=\{d_i\}i=1,\ldots,m$$

a set of symptoms is given by:

$$S=\{s_j\}j=1,\ldots,n$$

Further, a disjunction of S into three sets, present symptoms $S_{present}$ open symptoms $S_{open}$ and absent symptoms $S_{absent}$ is given by:

$$S=S_{present}\dot{\cup}S_{open}\dot{\cup}S_{absent}$$

For some disease d∈D the set of related symptoms is denoted by $S(d)\subseteq S$.

With respect to the ranking of diseases, all present symptoms which are in S(d), support a disease d, whereas absent symptoms of S(d) degrade the disease d.

In FIG. 1, symptoms $S(d)\cap S_{present}=\{s_1,s_3\}$ support disease d, whereas symptoms $S(d_1)\cap S_{absent}=\{s_2\}$ degrade disease d.

Because absent symptoms allow clinicians to exclude certain diseases, they are important in the diagnosis process. For example, a patient having a normal amount of leukocytes, erythrocytes and thrombocytes is very unlikely to have lymphatic or myeloic leukemia. A ranking of a particular disease increases with a greater amount of present diseases and with a less amount of absent symptoms matching the particular disease. The amount of open symptoms of S(d) expresses the grade of certainty of the judgement of d.

In the following, disease-specific factors are described.

The most distinctive disease-specific factor is the incidence proportion of a disease, which is the number of new cases within a specified time period divided by the size of the population initially at risk. With a normalized time period the incidence proportion can be used as the basic probability of a random person to be affected by a disease. However, for many diseases, even age- and gender-specific incidence proportions are available and even annually actualized.

The incidence proportion of a disease d∈D normalized to a time period of one year is given by P(d). The patient-specific incidence proportion of a disease d∈D respecting at least the patient's age and gender, normalized to a time period of one year, is denoted by $P_p(d)$.

Other patient-specific risk factors with influence on the incidence proportion like former diseases or the patient's life-style (smoking etc.), can be included in $P_p(d)$ if said risk factors are available.

In the following, disease-symptom-relations are described.

In order to infer likely diseases, information about their relation to symptoms is needed. In common medical text books, symptoms of diseases are well documented. In other words, the quantity S(d) is known. However, the strength of the relation is less well and less precisely documented. One would like to know a conditional probability of a disease depending on a particular symptom, P(d|s). However, this conditional probability is not available in most cases. Instead of a precise significance value, clinicians consider so called leading symptoms of a disease, which have a more significant relation to the respective disease than other symptoms. Further, the conditional probability of a symptom depending on a particular disease—P(s|d)—also contributes to the strength of the disease-symptom relation.

For all symptoms $s \in S$ and all diseases $d \in D$ a value $rel(s,d) \in [0,3]$ is defined which is describing the relatedness of d and s. Two factors contribute to $rel(s,d)$: the conditional probability $P(s|d) \in [0,1]$ and a factor for leading symptoms $l(s,d) \in \{1, 3\}$ (where $l(s,d)=3$ if s is a leading symptom of d, otherwise $l(s,d)=1$). The relatedness of s and d is then defined as $$rel(s,d) := P(s|d) \cdot l(s,d)$$

Setting the factor for leading symptoms to 3 can be understood only as a rule of thumb. To motivate this value, consider e.g. pulmonary embolism: a leading symptom is a suddenly appeared dyspnoea, however other symptoms like thoracic pain, raised D-dimer concentration and expectoration of blood, even though unspecific as single symptoms, in combination the three will make a clinician to think also at pulmonary embolism. Another example would be to consider the three unspecific symptoms fever, night sweats and weight loss. The presence all three is referred to as B-symptomatic, a leading symptom with high prognostic significance for Hodgkin's- and non-Hodgkin's lymphoma.

In the following, symptom specific factors are described.

Weighting symptoms and thus defining their relative importance is typically essential in diagnosis. However, such a definition is difficult since the clinician's experience and intuition is involved in several ways.

Hereinafter, all factors contributing to an importance of a certain symptom are defined. Usually, symptoms significantly differ in their default or basic importance and their need to be explained. The default importance factor represents the common importance value of a particular disease without consideration of any influencing context factors. E.g., the symptom "blood in stool" is intrinsically more critical than "feeling powerless".

For all symptoms $s \in S$ the default importance is defined by $\omega_{default}(s) \in (0,1]$.

The default importance is defined for all symptoms $s \in S$. In a first attempt, symptom-groups of similar importance are formed in order to ease a knowledge gathering.

For present symptoms $s \in S_{present}$ a number of additional factors are decisive, e.g. an intensity of a symptom.

For all symptoms $s \in S_{present}$ the intensity is given by $i(s) \in (0,1]$, where $i(s)=1$ if the symptom is present with full intensity.

Often, the intensity of symptoms is determined by a vague terminology using attributes like low, medium, high. Such intensity attributes have to be mapped to the interval $(0,1]$. E.g., lymph node enlargements are distinguished with respect to the amount of enlarged lymph nodes in "1, 2, many" so that i (many enlarged lymph nodes) would be set to one. For general intensity descriptions like "low", "medium" etc., standard values are used to ensure consistency.

Clinicians make a distinction between "newly appeared" and "old" symptoms. In their decision-making new symptoms are significantly more important than old ones. Consider, e.g., a patient having raised blood-pressure over some years already. If this patient consults a clinician with the symptoms of acute fever and lymph node enlargements, these symptoms are considered of being more important than the raised blood pressure. On the other hand, with respect to pulmonary embolism, a deep vein thrombosis has to be considered even if the patient has been affected for a long time already. This is why an integrated view on the patient's symptoms is of the essence, not only considering recently appeared symptoms.

For all symptoms $s \in S_{present}$ the novelty is defined by $n(s) \in \{1,3\}$, where $n(s)=3$ if the symptom is new and $n(s)=1$ otherwise.

In order to apply the novelty-factor, one has to define for each symptoms s a time-threshold t up to which the symptom is classified as new. Additionally to those factors, the clinician is optionally allowed by the method disclosed herein to influence the importance of symptoms within a certain range:

For this purpose a clinicians factor $c(s) \in [0,2]$ is defined according to an embodiment, the clinicians factor having default value of $c(s)=1$ if no influence from clinician's side was taken.

The clinician's factor can be used for both reducing and enhancing the importance. Setting the clinicians factor $c(s)$ to a value of zero, a present symptom can be disregarded in the ranking. Consider a patient with chronic thoracic pain. A newly appeared cough might be disregarded in the actual diagnosis setting $c(cough)=0$. However another clinician, suspecting pulmonary embolism, could enhance the importance of the cough setting $c(cough)=2$. The overall importance of a symptom s is then, according to one embodiment, defined as the product of the different factors:

The importance of a symptom $s \in S$ is denoted by $\omega(s)$. For $s \in S_{present}$ the weighting factor $\omega(s)$ regarding the significase is defined as $$\omega(s) := \omega_{default}(s) \cdot (1+i(s)) \cdot n(s) \cdot c(s), \forall s \in S_{present}$$

Intensity, novelty and clinician's factor are only applied for present symptoms. For all other symptoms $s \in S \setminus S_{present}$ $\omega(s)$ is defined as $$\omega(s) := \omega_{default}(s), \forall s \in S \setminus S_{present}$$

Note that for unchanged clinician's value $c(s)$, the following applies $\omega(s) > \omega_{default}(s)$, so that the symptom's importance is always higher in the case of present symptoms than in the case where the questioned symptom is absent.

In summary, according to one embodiment, three weighting factors are influencing the relationship between the plurality of symptoms and the plurality of diseases:

the patient-specific incidence of a disease $P_p(d)$;

the relatedness value for the disease-symptom relation $rel(s,d)$; and;

the symptom's weight $\omega(s)$ describing the importance of the symptom.

Figure 2:
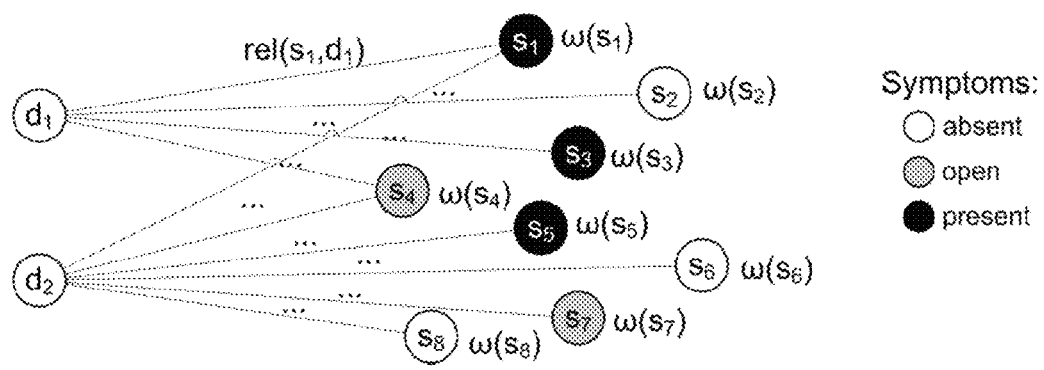
FIG. 2 shows a schematic representation of a multi-tier relationship between a plurality of symptoms and a plurality of diseases.

FIG. 2 shows a bipartite graph with weighted edges and nodes, wherein a partition on the left of FIG. 2 side represents the diseases plane and the opposite partition on the right side represents the symptoms plane.

The disease-symptom graph according to FIG. 2 is used as input for ranking likely diseases based on precision and recall. Within the graph, $s_1$, $s_3$ and $s_5$ are considered to be relevant, whereas $s_5$, $s_6$ and $s_8$ are retrieved by disease $d2$.

A first weighting factor $\omega(s_i)$ represents the importance of a symptom $s_i$, a second weighting factor represents the strength of the relation by $rel(s_i, d_j)$, which is exemplarily shown for $rel(s_1, d_1)$. A further weighting factor, the patient-specific incidence of a disease $P_p(d)$, is assigned to a corresponding disease node, which is not shown in FIG. 2.

The symptoms shown in FIG. 2 are marked as present, open or absent in dependence of the patient's situation. As explained above, present symptoms are supporting the related diseases, whereas absent symptoms are degrading the related diseases. The stronger the disease-symptom-relation is and the more important a symptom is the higher impact is affected towards an up-ranking of a respective disease.

The ranking of likely diseases may be realized in terms of precision and recall. This ranking, which means computing the most relevant disease for a given patient, extends the classical information retrieval approach. That is, in some embodiments of the method, the ranking relies on weighting factors assigned to edges and nodes of the disease-symptom model in order to infer the rank of the associated diseases.

Figure 3:
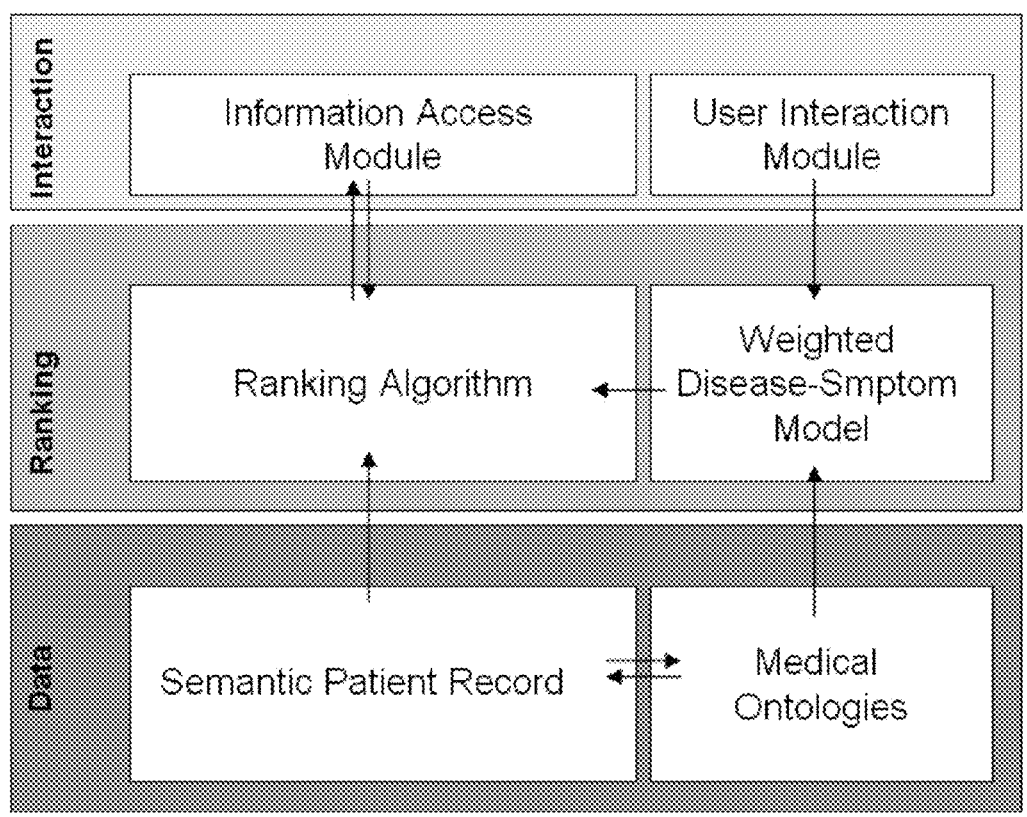
FIG. 3 shows a structural view of functional components of a system according to one embodiment.

FIG. 3 shows a structural view of functional components of a system according to an embodiment. The functional components are structured in three layers captioned interaction, ranking and data.

Within the data layer, a module captioned "Semantic Patient Record" is provided. This module encompasses the semantically annotated patient data.

A further module within the data layer and captioned "Medical Ontologies" stores all medical ontologies that are used for annotating the patient's data as well as adjusting the disease-symptom model and thus—intrinsically—enhancing the ranking algorithm by providing structural and relational information about medical diseases and symptoms.

Within the ranking layer, a module captioned "Ranking Algorithm" is provided which extends the classical information-retrieval approach and provides the basis for the efficient information access as well as means for the seamless incorporation of the mentioned context information.

A further module within the ranking layer and captioned "Weighted Disease-Symptom Model" consists of a knowledge model which primarily captures semantic relationships between disease and symptom information. In addition, the disease-symptom models represent the mentioned context parameters as dedicated weighting factors within the model, i.e.

- Disease specific information is represented by a weighting factor assigned to a corresponding disease node;
- Information about disease-symptom relationship is represented by a weighting factor assigned to edges connecting the respective disease nodes and symptom nodes; and;
- Symptom specific information is represented by a weighting factor assigned to corresponding symptom nodes.

Within the interaction layer, a module captioned "User Interaction Module" allows a user, e.g. a clinician, to adjust or fine-tune weighting factors according to her or his expertise and experience.

A further module within the interaction layer and captioned "Information Access Module" allows the user to access the disease information for a particular patient. Information access module can be enhanced by any kind of visualization mechanism that allows clearly arranged patient information being associated with the high-ranked disease.

The systems and methods disclosed herein may allow context-dependent ranking of disease information for a particular patient. Information about highly ranked disease can optionally be re-used for patient data visualization modules as part of a clinical diagnose support system.

The methods disclosed herein can be implemented in form of a separate application or as a part of a complex system. The implementation can be realized on any system ranging from personal computers to mobile devices with the special focus on dedicated mobile healthcare and service support devices.

Embodiments can be implemented in computing hardware (computing apparatus) and/or software, including but not limited to any computer or microcomputer that can store, retrieve, process and/or output data and/or communicate with other computers.

The processes can also be distributed via, for example, downloading over a network such as the Internet. A program/software implementing the embodiments may be recorded on computer-readable media comprising computer-readable recording media. The program/software implementing the embodiments may also be transmitted over a transmission communication media such as a carrier wave.

The invention has been described in detail with particular reference to preferred embodiments thereof and examples, but it will be understood that variations and modifications can be effected within the spirit and scope of the invention covered by the claims.

What is claimed is:

1. An automated method for supporting a clinical diagnosis for a patient, comprising:
   receiving, by a processor, patient-specific information regarding a plurality of symptoms associated with one or more of a plurality of diseases, wherein the patient-specific information regarding the plurality of symptoms categorizes each of a first subset of the plurality of symptoms as a present symptom determined as being present in the patient, and categorizes each of a second subset of the plurality of symptoms as an absent symptom determined as being absent in the patient;
   storing in memory the patient-specific information regarding the plurality of symptoms associated with the patient;
   the processor establishing or accessing a multi-tier relationship between said plurality of symptoms and the plurality of diseases defining, for each disease, one or more of the plurality of symptoms that match that disease;
   the processor adjusting at least one weighting factor for at least one (a) at least one of said multi-tier relationships and (b) at least one of said symptoms, based on a knowledge model; and
   the processor building a ranking of diseases from said multi-tier relationship based on said weighting factors and said patient-specific information regarding the plurality of symptoms;
   wherein for each respective disease, the number of symptoms categorized as present symptoms for the patient that match the respective disease, as defined by the multi-tier relationship, increases the ranking of the respective disease; and
   wherein the number of symptoms categorized as absent symptoms for the patient that match the respective disease, as defined by the multi-tier relationship, decreases the ranking of the respective disease.

2. The method of claim 1, wherein said multi-tier relationship between said plurality of symptoms and said plurality of diseases is implemented by a bipartite graph, the bipartite graph including a plurality of nodes with each node assigned to a symptom or disease, the bipartite graph including a plurality of edges expressing a particular relationship between a particular symptom and a particular disease.

3. The method of claim 1, wherein said weighting factors include at least one of a consideration of a patient-specific incidence of a disease, a strength of a disease-symptom relation, and an importance of a symptom.

4. The method of claim 1, wherein the received patient-specific information regarding the plurality of symptoms categorizes each of a third subset of the plurality of symptoms as an open system not determined as being present or absent in the patient.

5. A system for supporting a clinical diagnosis, the system comprising:

a patient record configured to receive and store patient-specific information regarding a plurality of symptoms associated with a patient, wherein the patient-specific information regarding the plurality of symptoms categorizes each of a first subset of the plurality of symptoms as a present symptom determined as being present in the patient, and categorizes each of a second subset of the plurality of symptoms as an absent symptom determined as being absent in the patient;

a weighted disease-symptom module including a knowledge model defining a multi-tier relationship between said plurality of symptoms and a plurality of diseases, the multi-tier relationship defining, for each disease, one or more of the plurality of symptoms that match that disease;

the weighted disease-symptom module configured to adjust at least one weighting factor for at least one (a) at least one of said multi-tier relationships and (b) at least one of said symptoms, based on a medical ontology module;

the weighted disease-symptom module configured to generate a ranking of diseases from said multi-tier relationship weighted by said weighting factors and said patient-specific information regarding the plurality of symptoms;

wherein for each respective disease, the number of symptoms categorized as present symptoms for the patient that match the respective disease, as defined by the multi-tier relationship, increases the ranking of the respective disease; and wherein the number of symptoms categorized as absent symptoms for the patient that match the respective disease, as defined by the multi-tier relationship, decreases the ranking of the respective disease; and wherein the weighted disease-symptom module is embodied by software stored in a non-transitory computer-readable medium and executable by a processor.

6. The system of claim 5, wherein the patient-specific information received and stored in the patient record module categorizes each of a third subset of the plurality of symptoms as an open system not determined as being present or absent in the patient.

* * * * *